(12) United States Patent
Walter et al.

(10) Patent No.: US 6,399,804 B2
(45) Date of Patent: Jun. 4, 2002

(54) METHOD FOR PRODUCING [IR(COD)CL]$_2$

(75) Inventors: Richard Walter, Alzenau; Sonja Kirchner, Bad Soden-Salmünster; Renate Franz, Gelnhausen, all of (DE)

(73) Assignee: W.C. Heraeus GmbH & Co. KG, Hanau (DE)

( * ) Notice: Subject to any disclaimer, the term of this patent is extended or adjusted under 35 U.S.C. 154(b) by 0 days.

(21) Appl. No.: 09/757,133

(22) Filed: Jan. 9, 2001

(30) Foreign Application Priority Data

Jan. 10, 2000 (DE) ......................................... 100 00 710

(51) Int. Cl.$^7$ ................................................. C07F 15/00
(52) U.S. Cl. ....................................................... 556/136
(58) Field of Search ......................................... 556/136

(56) References Cited

U.S. PATENT DOCUMENTS 6,197,716 B1 * 3/2001 Baumeister et al. .... 556/136 X

OTHER PUBLICATIONS

Inorganic Syntheses, vol. XV (1974), pp. 18–20.
Inorganic Syntheses, vol. XIV (1973), pp. 92–95.
Journal of Organometallic chemistry, 135 (1977), pp. 395–403.
Chemische Berichte, 99. Jahrg./1966/Nr. 10, pp. 3610–3619.
Chemical Abstracts, vol. 97, 1982, p. 668.

* cited by examiner

*Primary Examiner*—Paul F. Shaver
(74) *Attorney, Agent, or Firm*—Norris McLaughlin & Marcus

(57) ABSTRACT

A method for producing [Ir(cod)Cl]$_2$ is proposed, involving
a) Dissolving IrCl$_4$.nH$_2$O and/or IrCl$_3$.nH$_2$O and/or H$_2$IrCl$_6$ in water;
b) Adding an alcohol and cycloocta-1,5-diene and
c) Stirring the solution at the boiling temperature, characterized in that in step b) at least one alcohol is used having the formula R—OH wherein R=C$_n$H$_{2n+1}$ and n=3–9, especially isopropanol.

9 Claims, No Drawings

METHOD FOR PRODUCING [IR(COD)CL]$_2$

The invention relates to a method for producing [Ir(cod)Cl]$_2$.

In the state of the art there are known several methods for producing [Ir(cod)Cl]$_2$, namely by the methods of Herde (J. L. Herde, J. C. Lambert and C. V. Senoff: Inorganic Syntheses, 15 (1974), 18), Crabtree (R. H. Crabtree and G. E. Morris, J. Organomet. Chem., 135, 395 (1977), Winkhaus and Singer (Günter Winkhaus, Hellmut Singer, Chem. Ber., 99 (1966) 3610), Pannetier, Bonnaire and Fougeroux (G. Pannetier, R. Bonnaire et P. Fougeroux, Journal of the Less-Common Metals, 21 91970), 437–438), and Bezman, Bird, Fraser and Osborn (S. A. Benzman, P. H. Bird, A. R. Fraser, J. A. Osborn, Inorganic Chemistry, 12, 1980, 3755).

Winkhaus and Singer obtained [Ir(cod)Cl]$_2$ in a 45% yield by reacting Na$_2$IrCl$_8$.6H$_2$O or H$_2$IrCl$_8$.6H$_2$O with cod in a mixture of water and ethanol after 8 to 12 hours of heating with refluxing. After the precipitated crystals were washed with methanol the compound was dried and redissolved in dichloromethane.

Pannetier, Bonnaire and Fougeroux obtained the complex in a yield of 85% by reacting H$_2$IrCl$_6$ with cod in a mixture of water and ethanol after refluxing for 12 hours (no further information regarding the method of procedure).

Bezman, Bird, Fraser and Osborn describe the synthesis of [Ir(cod)Cl]$_2$ by a modified method of Winkhaus and Singer. Iridium trichloride hydrate, hydroquinone, ethanol, water and cycloocta-1,5-diene are refluxed for 4 hours. Then the solvent is partially distilled out and the precipitated product is filtered out, washed and dried. The yield is only 59%.

In Herde's method, iridium trichloride hydrate, ethanol, water and cycloocta-1,5-diene is refluxed for 12 hours. After cooling to room temperature the precipitated product is filtered out, washed and dried. A disadvantage of this method is the low yield of only 72%.

[Ir(cod)Cl]$_2$ is prepared by the Crabtree method, at first without the addition of water, and is then converted with aqueous sodium acetate to the desired complex compound, which is then recrystallized out of dichloromethane/ethanol. The yield in this case is 90–95%, but it entails a multi-step procedure which is therefore complicated and expensive.

From what as been stated, the problem arises of at least partially eliminating the above-stated disadvantages by means of a novel process. The present problem consists especially in offering a simple and thus less expensive method for the production of [Ir(cod)Cl]$_2$ in a high yield.

This problem is solved according to the invention by a method according to claim 1.

In the method of the invention, first IrCl$_4$.nH$_2$O and/or IrCl$_3$.nH$_2$O and/or H$_2$IrCl$_6$ are dissolved in water, then at least one alcohol of the formula R—OH wherein R=C$_n$H$_{2n+1}$ and n=3–9, especially isopropanol, and cod (cycloocta-1,5-diene) are added and the solution is stirred at the boiling temperature.

Important to the invention in the proposed method is the use of at least one alcohol of the formula R—OH wherein R=C$_n$H$_{2n+1}$ and n=3–9, especially isopropanol, which surprisingly in combination with water and cod has both good solvent properties as well as gives excellent precipitation of the end product. (The alkyl moieties of the alcohol are both straight-chain and branched moieties.)

The ordinary use of ethanol in the Herde process gives considerably lower yields (72%).

First, it is advantageous if the volumetric ratio of alcohol, especially isopropanol, to water is 2:1 to 1:1, since this ratio has proven good in practice both in regard to the solubility properties of iridium chloride, especially of IrCl$_4$, and also in regard to the excellent properties of precipitation of the end product.

It is furthermore advantageous if the molecular ratio of iridium to cod is 1:8.6, since this ratio has proven good in practice.

After the solution is stirred at ebullition the resultant [Ir(cod)Cl]$_2$ is filtered out, washed and dried, the solution as a rule being first cooled to room temperature. Such a procedure permits an excellent separation of the [Ir(cod)Cl]$_2$ from the solution.

It is furthermore advantageous, since it has been proved, if the filter cake (the desired end product) is washed with methanol, especially with cold methanol, and then dried.

Lastly, the residual solution freed from the precipitate is again concentrated in an advantageous manner, to about 30 to 50% of its original volume and the precipitate obtained is again filtered out, washed and dried, in order thus to increase the total yield.

It is furthermore advantageous if the [Ir(cod)Cl]$_2$ product is ground to a maximum grain size of about 0.4 mm, since this coarse powder has good handling properties, such as a satisfactory weigh-out ability.

The following examples serve to explain the invention:

EXAMPLE 1

10 g of iridium in the form of IrCl$_4$.nH$_2$O was dissolved in distilled water. Then 312 ml of isopropanol and 55 ml of cod were added portion-wise and stirred at ebullition for about 19 hours. This resulted in a color change from brown toward an intense red. The reaction itself was performed under inert gas (in this case argon). Upon cooling to room temperature, shiny red crystals of [Ir(cod)Cl]$_2$ precipitated, which were then filtered out and washed with a little cold methanol and dried. The yield was 8.27 g of solid, which corresponds to about 47.4%.

The filtrate solution was concentrated to about 30%, and again a bright red solid precipitated which was likewise filtered, washed and dried. Thus 7.34 g of the desired product was obtained (42.1% yield).

The total yield thus amounted to about 90%.

EXAMPLE 2

10 g of iridium in the form of IrCl$_4$.nH$_2$O was dissolved in 150 ml of distilled water. Then 312 ml of isopropanol and 55 ml cod were added portion-wise, and stirred for about 6 hours. A color change occurred, from brown toward an intense red. The reaction itself was performed under inert gas (nitrogen in this case). The solution was concentrated to about 50% of its original volume. [Ir(cod)Cl]$_2$ crystals precipitated, which were then filtered out and washed with a little cold methanol and dried. The yield of solids was 16.23 g (about 93%).

The product obtained was rolled in a ball mill so that the crystal size was less than 0.4 mm.

What is claimed is:

1. Method for the preparation of [Ir(cod)Cl]$_2$, by
   a) Dissolving IrCl$_4$.nH$_2$O and/or IrCl$_3$.nH$_2$O and/or H$_2$IrCl$_6$ in water,
   b) Adding an alcohol and cycloocta-1,5-diene and
   c) Stirring the solution at boiling temperature,
   characterized in that in step b) at least one alcohol is used of the formula R—OH, wherein R=C$_n$H$_{2n+1}$ and n=3–9.

2. Method according to claim 1, characterized in that in step b) isopropanol is used.

3. Method according to claim 1, characterized in that in step c) concentration is performed to about 30 to 50% of its original volume.

4. Method according to claim 1, characterized in that the volumetric ratio of alcohol, especially isopropanol, to water amounts to 2:1 to 1:1.

5. Method according to claim 1, characterized in that the molecular ratio of Ir to COD amounts to 1:7–9.

6. Method according to claim 1, characterized in that after step c) the [Ir(cod)Cl]$_2$ that has formed is filtered out, washed and dried.

7. Method according to claim 6, characterized in that the filter cake is washed with methanol and then dried.

8. Method according to claim 1, characterized in that the residual solution freed of the precipitate is again concentrated to about 30 to 50% of its original volume and the precipitate obtained is again filtered out, washed and dried.

9. Method according to claim 1, characterized in that the [Ir(cod)Cl]$_2$ product is ground to a maximum crystal size of about 0.4 mm.

* * * * *